United States Patent [19]

Purdie

[11] Patent Number: 5,252,488
[45] Date of Patent: *Oct. 12, 1993

[54] CIRCULAR DICHROISM AND SPECTROPHOTOMETRIC ABSORPTION DETECTION METHODS AND APPARATUS

[75] Inventor: Neil Purdie, Stillwater, Okla.

[73] Assignee: Research Corporation Technologies, Inc., Tucson, Ariz.

[*] Notice: The portion of the term of this patent subsequent to Sep. 21, 2010 has been disclaimed.

[21] Appl. No.: 785,998

[22] Filed: Oct. 31, 1991

Related U.S. Application Data

[63] Continuation-in-part of Ser. No. 639,222, Jan. 9, 1991, which is a continuation-in-part of Ser. No. 463,473, Jan. 11, 1990, abandoned.

[51] Int. Cl.$^5$ .................. G01N 21/19; G01N 33/52; G01N 33/92
[52] U.S. Cl. ...................... 436/71; 436/164; 436/161; 436/172; 356/39
[58] Field of Search ............ 436/71, 164, 171, 172; 435/11; 356/39, 222

[56] References Cited

PUBLICATIONS

Purdie et al. "Pobrimetry, Optical Rotating Dispersion, and Circular Dichroism", Anal. Chem., vol. 61, No. 2, pp. 77–89, 1989.
Chemical Abstract No. 210070, vol. 108, No. 24, (Jun. 1988).
Chemical Abstract No. 166955, vol. 98, No. 20 (May 1983).
Chemical Abstract No. 132207, vol. 84, No. 19, (May 1976).
Clinical Chemistry News, vol. 15, No. 9, Article by Laurent Posnick (1989).
Lambert et al., Org. Struct. Anal., Macmillan, N.Y. (1976), pp. 325–332.
Grahnen et al., Clinica Chimica Acta, 52 (1974), pp. 187–197.
Kannel et al., Annals of Int. Medicine, vol. 74, No. 1, (1971) pp. 1–12.
Castelli et al., JAMA, vol. 256, No. 20, (1986), pp. 2835–2838.
Abbott et al., Arteriosclerosis, vol. 3, No. 3, (May/Jun. 1983) pp. 260–272.
Clinical Chemistry, vol. 34, (1988), pp. 193–201.
Superko et al., JAMA, 256, No. 19 (Nov. 1986), pp. 2714–2717.
Warnick et al., Clinical Chemistry, vol. 26, No. 1, (1980) pp. 169–170.
Grundy et al., Arch. Intern. Med., vol. 149, (Mar. 1989), pp. 505–510.
Cox and Spencer, Canadian Journ. of Chemistry, vol. 29, pp. 217–222.
Baillie et al., 43rd Natl. Mtg. Am. Ass. for Clinical Chem., 1991, Workshop Report.
Warnick et al., 43rd Natl. Mtg. Am. Ass. for Clinical Chem., 1991, Roundtable Report.

Primary Examiner—James C. Housel
Assistant Examiner—David Redding
Attorney, Agent, or Firm—Birch, Stewart, Kolasch & Birch

[57] ABSTRACT

Spectrophotometric methods, including the use of circular dichroism, spectrophotometric absorption detection fluorescence and derivative spectrophotometric absorption methods for use in clinical chemistry detection methods. More specifically, with the use of such spectrophotometric methods in the measurement of cholesterol levels and direct measurement of cholesterol subfractions in test samples. The invention is also concerned with providing certain absorption detection spectrophotometric apparatus and spectrophotometric reagents useful in the aforesaid methods.

27 Claims, 13 Drawing Sheets

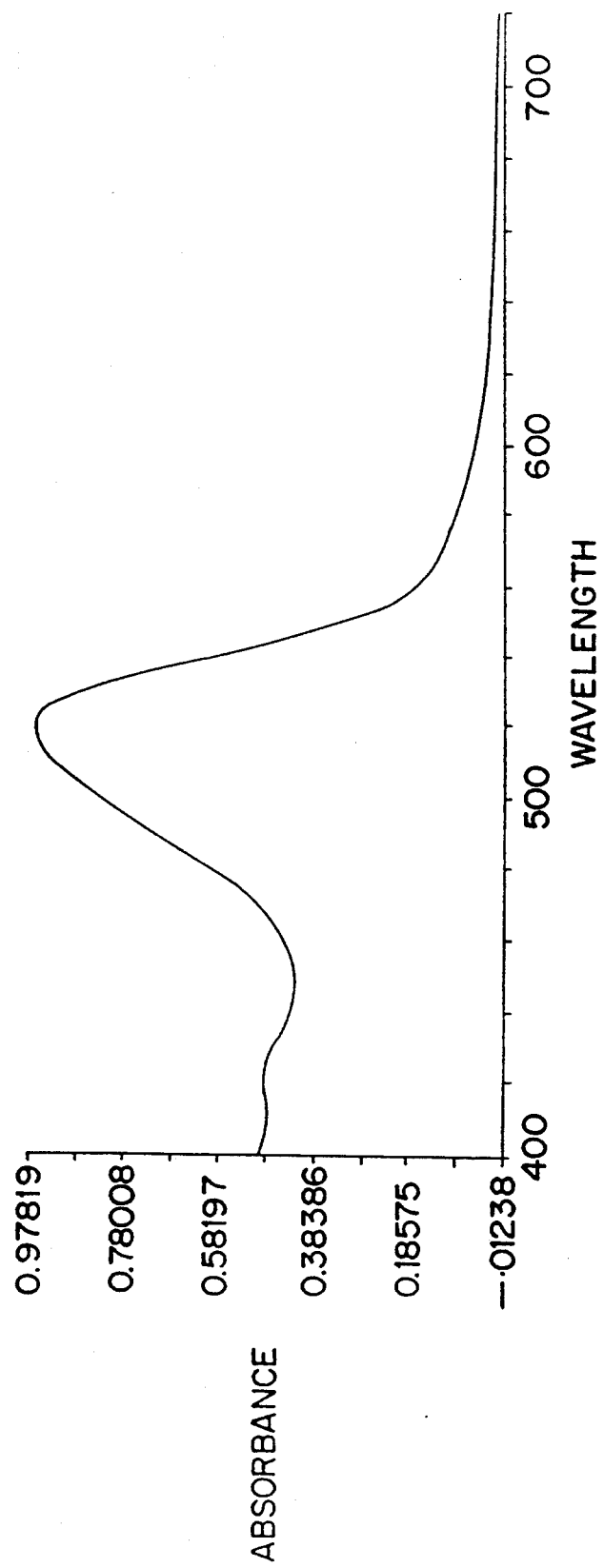

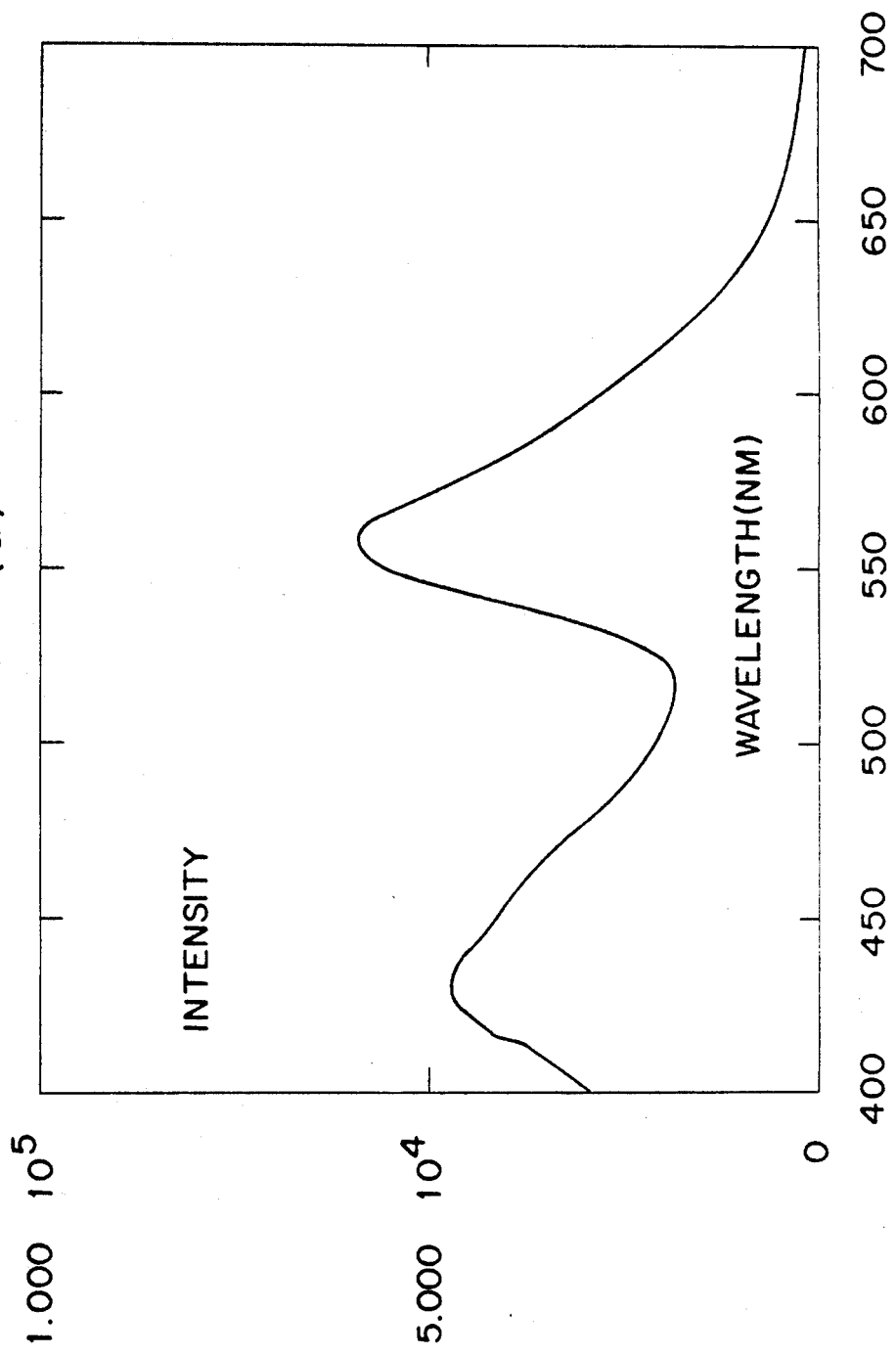

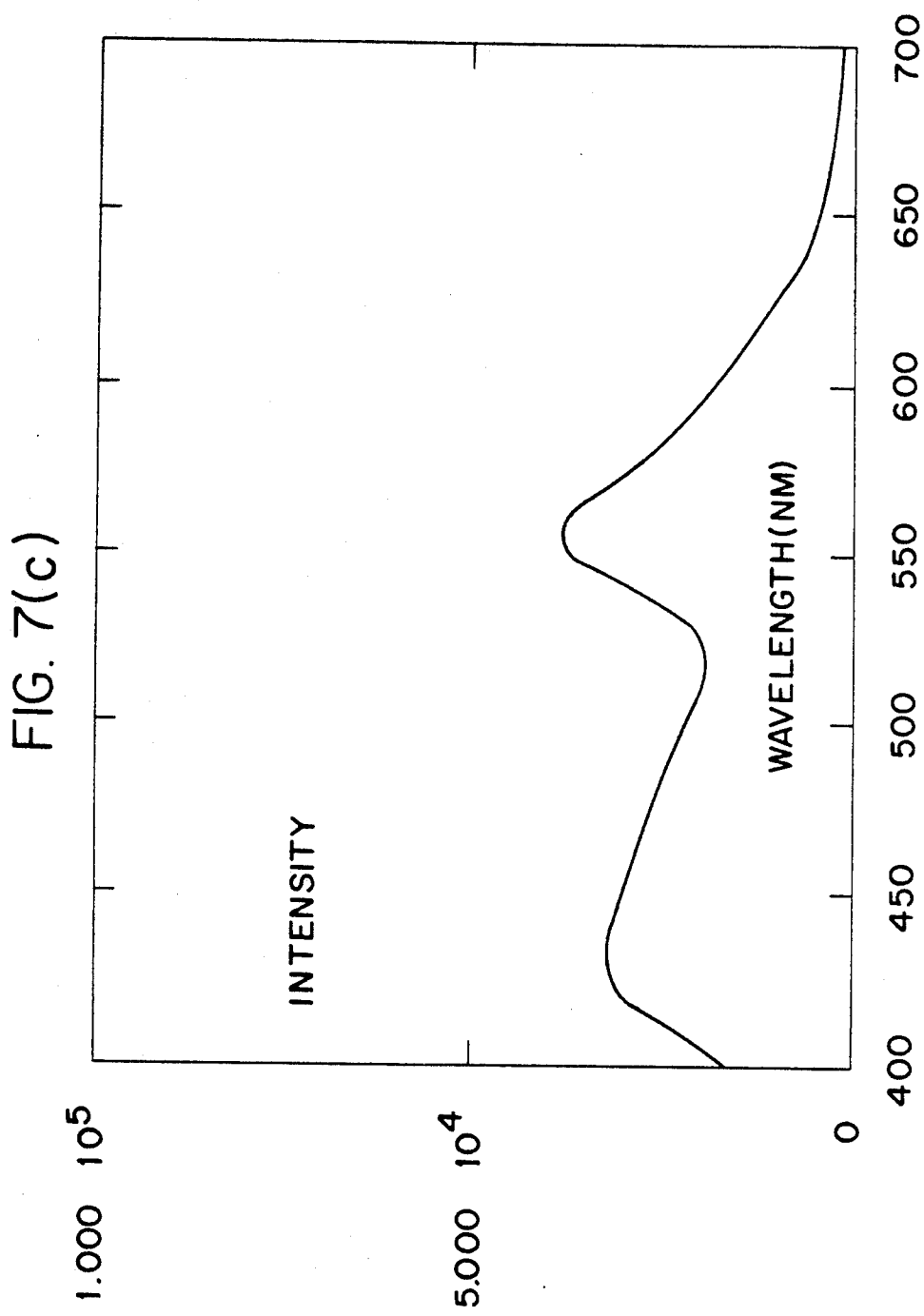

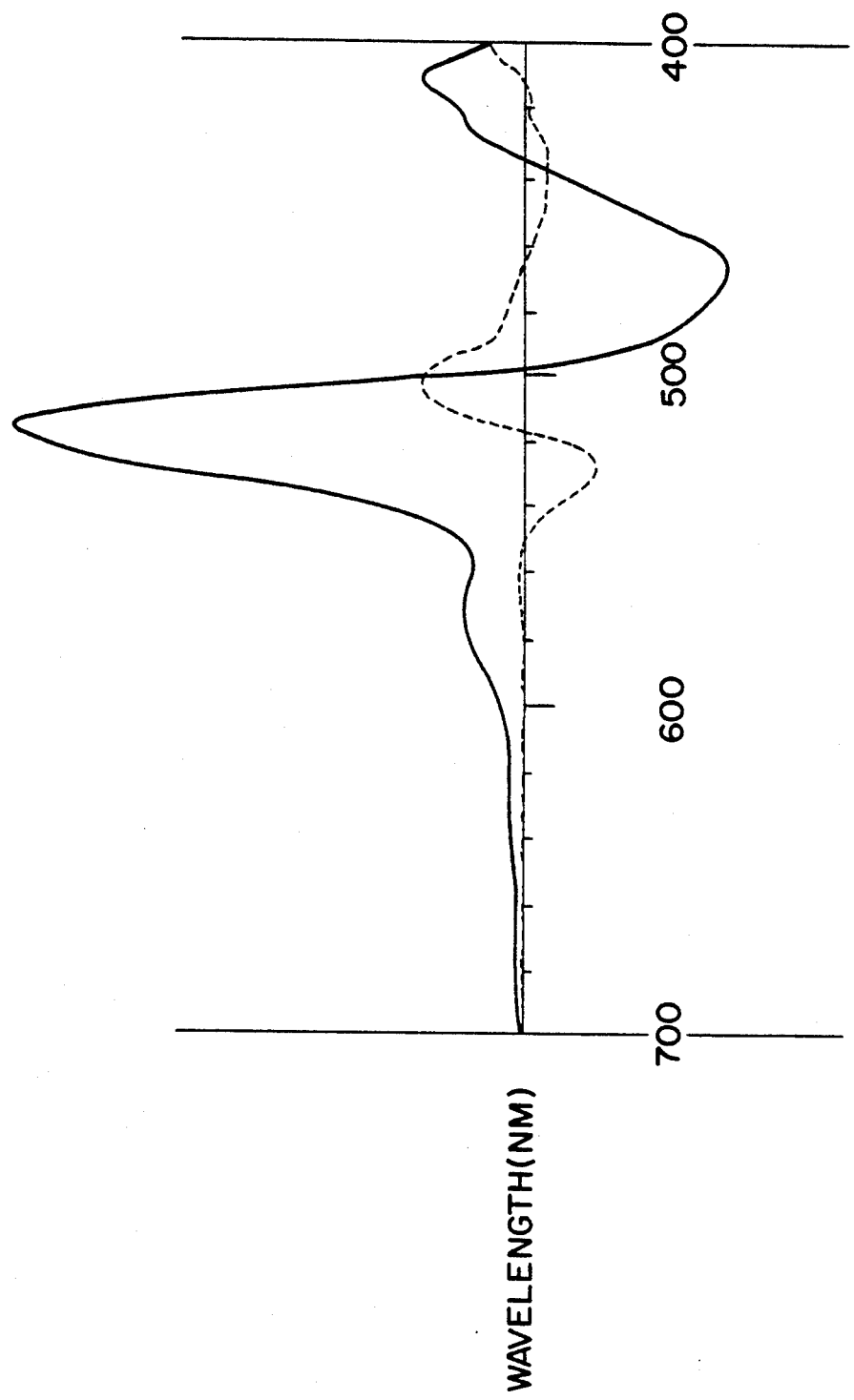

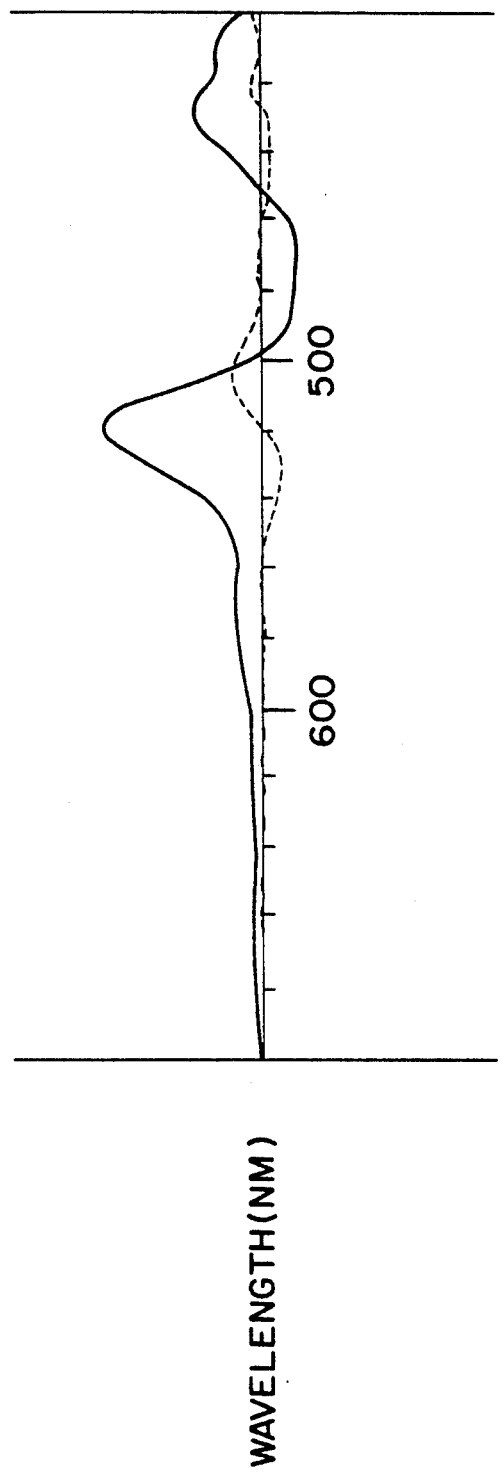

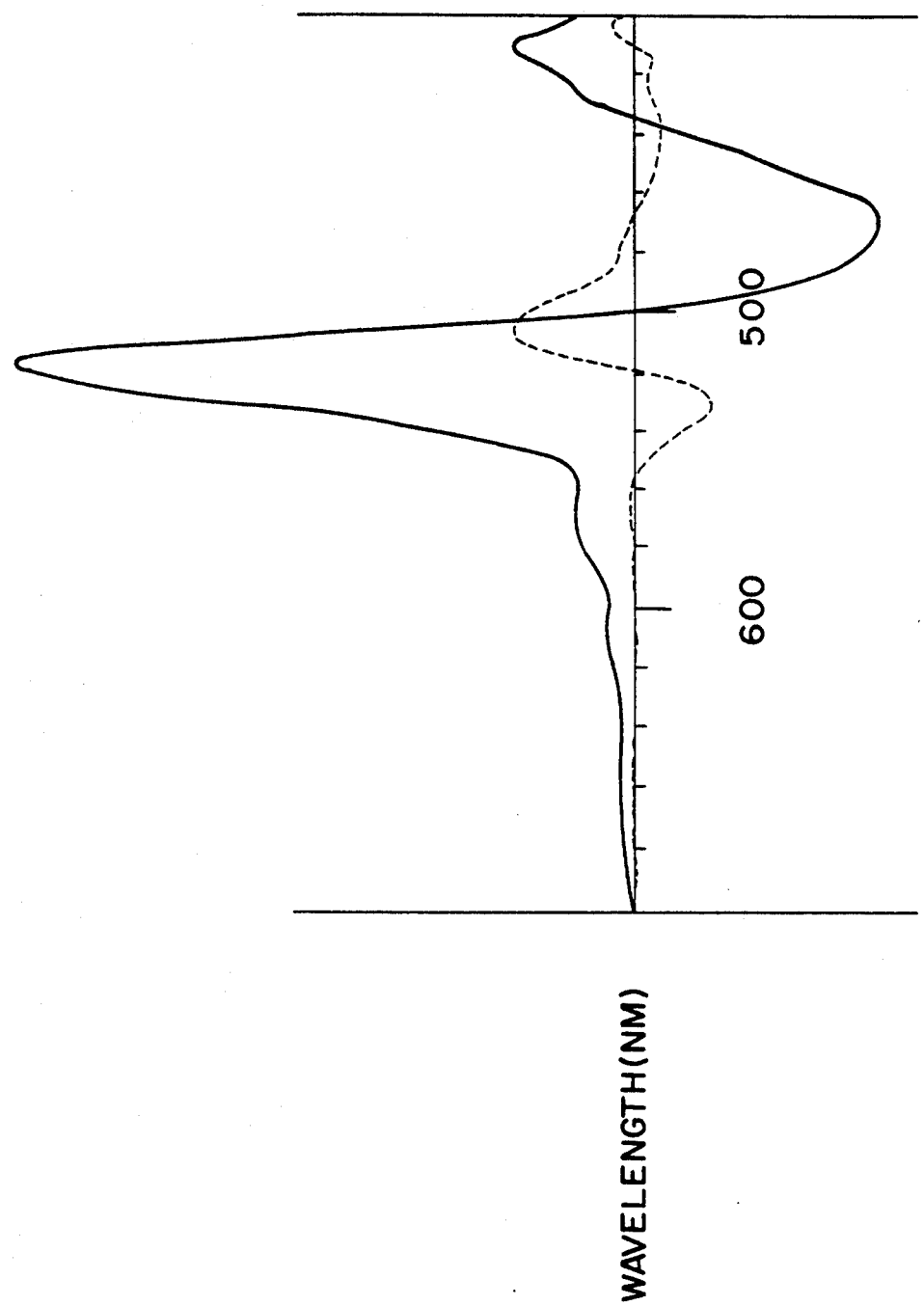

CIRCULAR DICHROISM AND SPECTROPHOTOMETRIC ABSORPTION DETECTION METHODS AND APPARATUS

The present application is a continuation-in-part application of copending U.S. application Ser. No. 07/639,222, filed on Jan. 9, 1991, which is a continuation-in-part application of copending U.S. application Ser. No. 07/463,473, filed on Jan. 11, 1990 (now abandoned); both of which prior applications are expressly incorporated herein by reference.

FIELD OF THE INVENTION

The present invention is concerned with the use of circular dichroism, absorption spectrophotometry, fluorescence spectrophotometry and derivative absorption spectrophotometry in clinical chemistry detection methods. More specifically, with their use in the measurement of cholesterol levels and direct measurement of total cholesterol and cholesterol subfractions in clinical samples. The invention is also concerned with providing a certain absorption detection apparatus useful in the aforesaid absorption detection chemical methods.

BACKGROUND OF THE INVENTION

Spectrophotometry refers to the measurement of the absorption or transmission of incident light through solutions of test compounds. Typically, compounds of interest have characteristic spectra, transmitting or absorbing specific wavelengths of light, which can be used to determine the presence of these compounds or measure their concentration in test samples. Instruments designed for spectrophotometric absorption have a light source, for which the emitted wavelength is known and may be adjusted, and one or more detectors sensitive to desired wavelengths of transmitted or reflected light. Spectrophotometric absorption can be used to determine the amount of a given compound that is present in a test sample.

Circular dichroism (CD) is a special type of absorption method in which the molecular composition of the analyte results in differential absorption of incident light not only at a specific wavelength but also of a particular polarization state. Circular dichroism is a chiroptical method which allows one to differentiate between different enantiomers, that is, optical isomers having one or more asymmetric carbon atom (chiral) centers. When utilizing CD, generally a sample is illuminated by two circularly polarized beams of light traveling in unison. Both beams pass through the sample simultaneously and are absorbed. If the sample is optically active, the beams are absorbed to different extents. The differences in absorption of the beams can then be displayed as a function of the wavelength of the incident light beam as a CD spectrum. No difference in absorption is observed for optically inactive absorbers so that these compounds are not detected by a CD detecting system. The use of CD as a chiroptical method has been fully described in scientific literature (1).

Early applications of the CD method primarily dealt with elucidation of molecular structures, especially natural products for which a technique capable of confirming or establishing absolute stereochemistry was critical. However, CD has also reportedly been used in a clinical method to quantitatively determine unconjugated bilirubin in blood plasma (2). In the method disclosed, a complex was formed between bilirubin and human serum albumin as a CD probe for bilirubin analysis.

Clinical applications of circular dichroism are also discussed by Neil Purdie and Kathy A. Swallows in *Analytical Chemistry*, Vol. 61, No. 2, pp 77A-89A (1989), herein incorporated by reference. Possible clinical applications of CD are disclosed to include measurement of cholesterol levels and detection of anabolic steroids. However, suitable chemical reagents for carrying out such testing are not disclosed.

Regarding the use of spectrophotometric absorption, fluorescence, derivative spectrophotometry or CD methods herein disclosed to measure cholesterol levels, it is noted that the population at large is continually advised that it is prudent to know serum cholesterol levels and constantly reminded that an uncontrolled diet and a lack of exercise can lead to accumulation of arterial plaque that will increase the risk of atherosclerosis and coronary heart disease. Statistical studies have shown that other risk factors, such as age, gender, heredity, tobacco and alcohol consumption, etc. must also be considered when counselling patients about the risks (3,4).

The magnitude of the program for screening the general public is so immense that automated methods for cholesterol determinations are necessary. The tests currently used differ in complexity from the simple dip-stick approach, which uses a color sensitive reaction on a paper support, to the sophisticated lipid profile tests, in which the distribution of cholesterol among the various solubilizing molecular species is determined (5). The dip-stick is only a preliminary qualitative test upon which a decision for the fuller, more quantitative measurement can be based.

At the conclusion of a recent extensive study of how health risk factors are related to elevated levels of serum cholesterol, a report (6) was prepared by the Laboratory Standardization Panel (LSP) of the National Cholesterol Education Program (NCEP) in which the measure of risk was correlated with three ranges of total cholesterol (TC): low risk if less than 200 mg/dL; moderate risk in the range 200-239 mg/dL; and high risk if greater than 240 mg/dL. In order to place a particular individual into one or other of these categories, all that is required is a serum TC measurement. The other risk factors (3,4) are then added as a basis for further patient counselling. This relatively simple approach replaces an earlier recommendation (3,7), in which relative risk was established using a ratio of TC to high density lipoprotein cholesterol (HDL-C) equal to 5. A ratio lower than 5 implies a high level of HDL-C and a low relative risk. For this diagnosis, HDL-C is measured in a second independent test.

The same report (6) hastened to add that there were serious inaccuracies in measurements made by numerous clinical laboratories in the determination of the amount of TC present in human serum reference standards.

Statistically the results showed that, in data from 1500 laboratories, 47% failed to measure the true value to within a coefficient of variance (CV) of ±5%, and 18% of these failed at a CV of ±10%. As a consequence, the LSP recommended that an improvement in CV to within ±3% for TC should be achieved by 1992. Recent surveys indicate that certified laboratories are well on their way to meeting that challenge, using the current clinical methods and instrumentation (8). The LSP did not report the inaccuracies associated with the determination of the distribution of cholesterol among the various lipids and lipoproteins, but did indicate that an evaluation would be made in the future. The very poor proficiency and lack of reliability in the measurement of serum or plasma HDL-C, has been eloquently described in three recent publications (7,9,10), where interlaboratory CV's as high as 38% were reported (9). A 1987 evaluation by the College of American Pathologists (CAP) of the measurement of the same sample for HDL-C by over two thousand laboratories showed, that more than one third differed by more than 5% from the reference value. Interlaboratory CV's among groups using the same method did improve to 16.5%, but it is still too imprecise to be of any predictive clinical value. This is the reason the TC:HDL-C ratio is no longer used in risk assessment, although it offers potential advantages in defining the true clinical picture.

Regarding the presently used lipid profile studies, cholesterol is distributed in the serum mainly associated with high density lipoprotein (HDL-C) and low density lipoprotein (LDL-C) fractions and with triglycerides as the very low density lipoprotein cholesterol (VLDL-C) fraction. There is plenty of statistical evidence from a number of long term clinical tests to justify that a high proportion of HDL-C and a low proportion of LDL-C is associated with lower relative risk (3,4) or in simpler terms, high levels of LDL-C are to be avoided where possible. HDL-C is beneficial, provided the level is not excessively low, i.e., less than 30 mg/dL (7). VLDL-C cholesterol has not been implicated in any risk determination, but high triglyceride itself can be a serious problem. In a typical lipid profile study, total cholesterols are measured directly and HDL-C is measured in the supernatant remaining after treatment of the sample with an agent to precipitate out LDL-C and VLDL-C. VLDL-C is taken to be a fixed fraction (e.g, 0.2) of the triglyceride, which is also measured directly in a separate assay. LDL-C is calculated from these figures and is not measured directly. The propagation of errors in each of the three independent measurements makes LDL-C the fraction known with least overall accuracy and precision, although it may be the most significant aspect of cardiovascular risk. Because of this, it is difficult to meaningfully monitor and justify that clinical progress has been made in LDL-C reduction therapy with time.

At a workshop and subsequent roundtable session (13,14) held at the 43rd Meeting of the American Association for Clinical Chemistry, the present state of the art in this area was summarized. It was concluded that accuracy is essential in HDL measurement. While presently available precipitation methods can give satisfactory results, the values obtained by these methods in routine clinical laboratory settings do not meet the real medical needs. The CAP comprehensive chemistry proficiency survey from 1982 to 1991 for HDL-C showed interlaboratory CVs of about 20% in 1991, with no overall improvement since 1982. The CVs delivered by clinical instruments used for HDL-C measurements ranged from 7.6% for the Dimension to 50% for the Ektachem. At the sessions, it was also noted that direct methods for LDL cholesterol are needed. The use of triglyceride determinations to estimate VLDL-C by the Friedewald equation is the method of choice now until better methods become available. To quote the workshop syllabus, "The variability typically observed in the measurement of total and HDL cholesterol and triglycerides may preclude attaining acceptable precision. In fact, to achieve the ideal precision in LDL cholesterol estimation, the precision of the constituent measurements must be better than their ideal specifications."

SUMMARY OF THE INVENTION

An object of the present invention is to provide spectrophotometric methods for direct measurement of cholesterol in clinical samples, as it exists in association with several particular lipoprotein subfractions. These spectrophotometric methods encompass CD, and conventional absorption, fluorescence and first and second derivative absorption spectrophotometries.

Another object of the present invention is to provide a method of measuring cholesterol levels in a clinical test sample, wherein the combined LDL-C+VLDL-C levels is determined directly by CD, or wherein VLDL-C, LDL-C and HDL-C levels are determined separately and directly, using absorption, fluorescence, or derivative absorption spectrophotometries. It is also an object of the present invention to provide novel spectrophotometric apparatuses to carry out absorption detection methods herein disclosed.

Accordingly, the present invention provides for a clinical method for determining the amount of cholesterol (in cholesterol subfractions) in a test sample, by forming a reaction product with the cholesterol and then either performing step ($a^1$), ($a^2$), ($a^3$) or ($a^4$), wherein steps ($a^3$) and ($a^4$) may be followed by calculation of cholesterol concentrations using matrix mathematics and constants derived for the particular cholesterol subfraction analyzed:

Step ($a^1$) determining the CD absorption spectrum of the test sample over a range from about 150 to 700 nm (preferably from about 360 nm to 700 nm);

Step ($a^2$) determining the CD absorption of the test sample at one or more discrete wavelengths within a range from about 150 to 700 nm (preferably from about 360 nm to 700 nm);

Step ($a^3$) determining the spectrophotometric, fluorescence or derivative spectrophotometric absorption of the test sample at three or more discrete wavelengths within a range from about 150 nm to 700 nm (preferably about 360 to 700 nm).

Step ($a^4$) determining the spectrophotometric, fluorescence or derivative spectrophotometric absorption of the test sample over a range from about 150 to 700 nm (preferably from about 360 nm to 700 nm).

The invention further provides novel absorption detection apparatuses for practicing certain of the present inventive methods, which apparatuses are exemplified, but not limited, by the following.

A spectrophotometric absorption instrument for determining the amount of VLDL-C, LDL-C, HDL-C and TC present in a test sample, the instrument comprising means for determining the spectrophotometric absorption spectrum of the test sample at 3 or more distinct wavelengths, within the range of about 150 to 700 nm (preferably 360–700 nm), and means for determining the amount of VLDL-C, LDL-C, HDL-C and TC present in the test sample based on the spectrophotometric absorption of the Chugaev reaction products in the test sample. Optionally, the instrument further comprises means for adding reagent to the test sample.

BRIEF DESCRIPTION OF THE DRAWINGS

The present invention will become more fully understood from the detailed description given here and below and the accompanying drawings which are given by way of illustration only, and thus, are not limitative of the present invention.

FIG. 6 is a graph of the absorption spectrum of whole serum over the wavelength range of 400–700 nm.

FIG. 7(a) is a graph of the fluorescence spectrum for VLDC-C subfraction;

FIG. 7(c) is a graph of the fluorescence spectrum of HDL-C subfraction;

FIG. 8(b) is a graph of the first (solid line) and second (dotted line) derivatives of the conventional absorbance spectrum of the LDL-C subfraction (sigma);

FIG. 8(c) is a graph of the first (solid line) and second (dotted line) derivatives of the conventional absorbance spectrum of the HDL-C subfraction (sigma);

FIG. 9(b) is a graph of the first (solid line) and second (dotted line) derivatives of a Serum B test sample.

DETAILED DESCRIPTION OF THE INVENTION

The following detailed description of the present invention is provided as an aid in the practice of the present invention. Much of the discussion appearing herein relates to methods and instruments for determining TC and the amount of cholesterol subfractions present in a test sample, however, the present invention should not be considered to be unduly limited by such discussions. This is true, since those skilled in the art will generally understand that the reagents, reagent ratios, reaction conditions and apparatuses herein disclosed may be modified without departing from the spirit or scope of the present invention.

The following discussion first provides a glossary of certain terms used herein, and then considers the inventive methods herein disclosed and concludes with a discussion of novel apparatus, which are particularly useful in performing the methods herein disclosed.

The following Glossary of Terms is provided to remove any ambiguity, which may exist as to the use of certain terms and abbreviations used herein.

Figure 5:
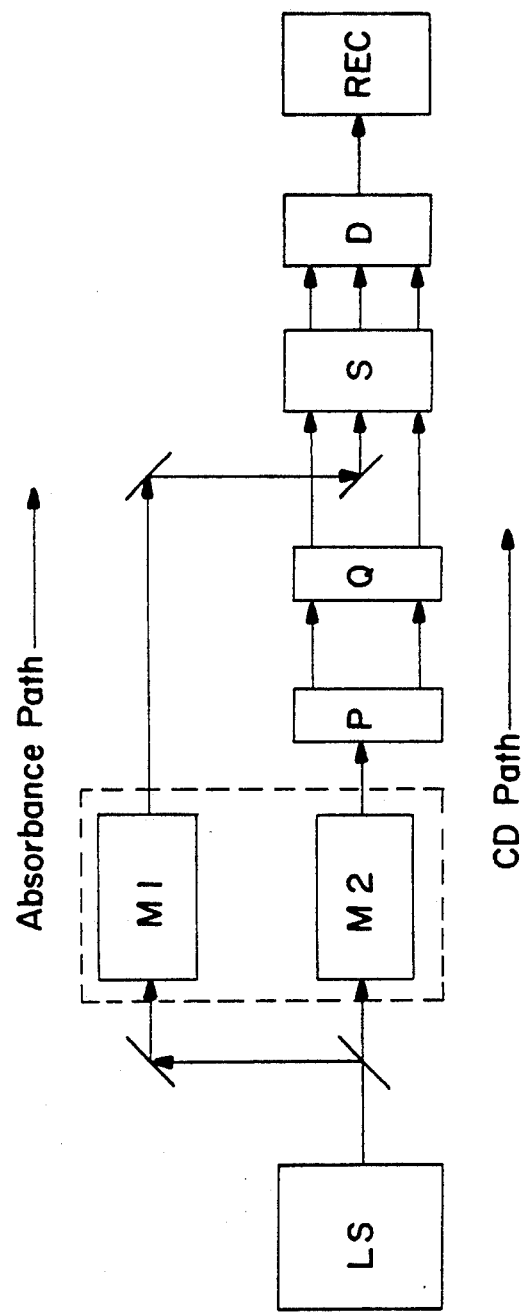
FIG. 5 is a schematic of a CD, wherein:
LS is the high intensity conventional light source or laser source; M1 and M2 are monochromators required for full spectral data; P is the linearly polarizing element; Q is the circularly polarizing element; S is the sample cell; D is the detector (of which there may be up to three); and REC is the recorder.

The term "CD instrument" as used herein, means a Circular Dichroism Instrument. Such instruments are available commercially or may be constructed from parts, which may be commercially available. Additionally, FIG. 5 is included herewith to provide a simple schematic of how a CD works. As can be seen in FIG. 5, light from a light source (LS) is linearly polarized with linear polarizers (P) and then circularly polarized in opposite directions by circular polarizers (Q) and then shown through a specimen cell (S), whereupon absorbance is measured by a detector (D), the difference in absorption of the oppositely polarized light beams is measured and plotted as a function of wavelength to produce a CD spectrum, or alternatively, may be recorded at preselected wavelengths.

The term "LDL cholesterol" (abbreviated LDL-C) as used herein, means low density lipoprotein cholesterol. The term "HDL cholesterol" (abbreviated HDL-C) as used herein, means high density lipoprotein cholesterol. The term "VLDL cholesterol" (abbreviated VLDL-C) as used herein, means very low density lipoprotein cholesterol, the abbreviation "(VLDL+LDL)-C" as used herein means the combined VLDL-C and LDL-C fractions and the term "total cholesterol" (abbreviated TC) as used herein, means the sum of the cholesterol subfractions in a test sample, i.e., TC=HDL-C+LDL-C+VLDL-C. The term "Cholesterol Subfraction" as used herein, refers to any or all of HDL-C, LDL-C and VLDL-C.

The term "Chugaev reagent" as used herein, means a reagent described by Cox and Spencer (11) or to reagents derived from that basic reagent configuration by varying the proportions of the acetyl chloride, zinc chloride and acetic acid, or by substituting zinc acetate in acetyl chloride for zinc chloride/acetic acid.

The term "Chugaev reaction product" as used herein, means any of the reaction product(s) of cholesterol with Chugaev reagents. A "Chugaev Reaction" utilized herein to form a Chugaev reaction product of the present invention, is discussed in the literature (11) and is thought to involve dehydration and opening of the B-ring of the steroid to form an optically active colored reaction product.

The term "test sample", "clinical test sample" or "serum test sample" as used herein, refers to a whole blood test sample or a whole blood test sample having the cell bodies removed therefrom by means which are well known to those skilled in the art (e.g., by centrifugal force, a filtering mechanism or the like).

The term "spectrophotometric absorption" as used herein refers to measurement of the absorption (or, conversely, transmission) of incident light by colored compounds at specific wavelengths, irrespective of the state of polarization of the light.

The term "spectrophotometric absorption detection" as used herein means detection and quantitation of analytes in a test sample by measuring their absorption of light at various wavelengths, without regard to the state of polarization of the incident or absorbed light. Absorption in this case is proportional to the number of molecules of analyte present in the test sample.

The term "fluorescence spectrophotometry" as used herein means detection and quantitation of analytes in a test sample by measuring the intensity of light emitted by the analytes at various wavelengths, following their irradiation by incident light at different wavelengths. Fluorescence is proportional to the number of molecules of analyte in the irradiated sample.

The term "first derivative spectrophotometry" as used herein describes the spectrum that is obtained by calculating the rate of change of absorbance with wavelength plotted against wavelength. The term "second derivative spectrophotometry" as used herein describes the spectrum obtained by calculating the rate of change of the first derivative with wavelength plotted against wavelength.

METHODS

Direct Detection of Cholesterol Fractions Using CD Absorption, Spectrophotometric Absorption Detection, or Fluorescence or Derivative Absorption Spectrophotometric Methods

A. Direct Detection Using CD

There are several advantages associated with the present invention which enable one skilled in the art to measure the high density cholesterol fractions in a direct manner with excellent precision. One of these advantages is the introduction of a color reaction described in the literature as the Chugaev reaction (11).

The reagents utilized in making the Chugaev reaction are for example 20% w/v $ZnCl_2$ in glacial acetic acid, and 98% acetyl chloride. These materials can be stored in separate containers and will remain usable for many weeks, even when stored at about 40° C. Moreover, the degree of their dryness does not have to be carefully controlled. The product of the Chugaev reaction with cholesterol is reddish orange in color and is thought to be a conjugated triene CD-active derivative of cholesterol. The intensity of the color is a direct measure of the cholesterol concentration. In contrast, dyes used in the present methods for cholesterol analysis are secondary products of cholesterol oxidation and are not derivatives of the cholesterol molecule itself. They are thus an indirect measure of the number of cholesterol molecules present in the test sample.

If desired, the components of the Chugaev reagent may also be stored together in a ratio over the range of about a 1:1 to 4:1 $ZnCl_2$/glacial acetic acid to 98% acetyl chloride, all of which gave satisfactory reactions with cholesterol. Reagents must be kept when stored under airtight conditions in an amber glass, teflon or a similar container. In this regard, an extended period of stability was observed for reactants stored together at 40° C. in amber bottles for at least 4 weeks.

It was observed that when ratios of 1:1 to 4:1 of zinc reagent to acetyl chloride are utilized, voluminous precipitates can occur, which cannot always be removed in a centrifugation step that follows the incubation period. While this is not a serious problem in CD detection, because the difference in absorption of two beams is measured which effectively cancels out the contribution from light scattering, it can be serious when a single beam absorption detection method is used (e.g., absorption detection, fluorescence or derivative absorption spectrophotometry). In this respect, the inventor has discovered that when the acetyl chloride is used in an amount in excess of the zinc reagent (e.g., 20%–25% w/v $ZnCl_2$ in glacial acetic acid) problems with precipitates are minimized. Most preferably the acetyl chloride is used in a high relative amount to the zinc reagent. Such preferred ratios range from about 4:1 to 100:1. Alternatively, zinc acetate may be added directly to the acetyl chloride, e.g., 0.95 mg zinc acetate dihydrate in 1.0 ml acetyl chloride.

An advantage when using CD in the present invention is that CD allows for great specificity and selectivity in determining the amount of the different cholesterol subfractions present in the test sample, i.e., (VLDL-C+LDL-C) and HDL-C. However, a drawback is that the levels of VLDL-C and LDL-C could not be directly separated using CD.

Figure 1:
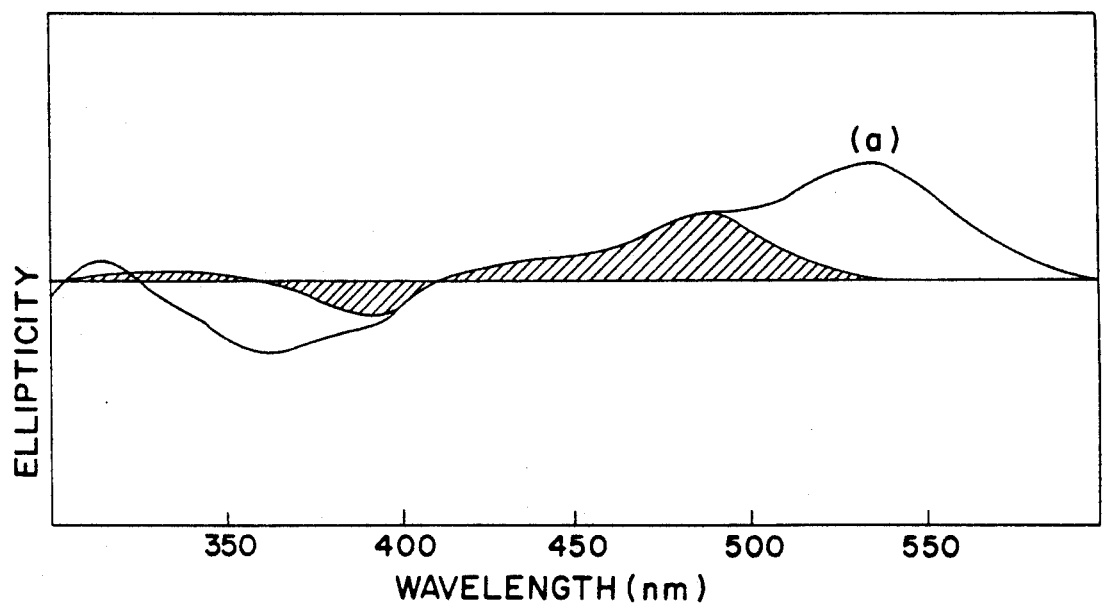
FIG. 1 is a full CD spectrum for the optically active colored product obtained from the reaction of Chugaev reagents with cholesterol. Curve (a) is representative of the total cholesterol, while the shaded area is the spectrum after the addition of the LDL-C/VLDL-C precipitating agent and is therefore representative of the HDL-C fraction only.

The full CD spectrum for the orange colored optically active product from the Chugaev reaction with cholesterol is shown in FIG. 1. The sample is a chloroform solution of the NBS Cholesterol Standard Reference Material (SRM911a). This spectrum is used as the reference standard for all subsequent serum cholesterol measurements.

In the CD absorption spectrum, the HDL-C and the (VLDL+LDL)-C fractions are associated with different spectral bands and can be measured directly from the same specimen, FIG. 1, without the need for a precipitation step to determine HDL-C. In this regard, measurements at 525 nm give results for the combined (VLDL-C+LDL-C) fractions and measurements at 390 nm (or preferably the algebraic sum of the negative and positive CD absorption peaks at 390 nm and 475 nm, respectively) give results for the HDL-C fraction.

It is thought preferable to determine the algebraic sum of the CD absorption peak heights at about 390 and 475 nm, when determining HDL-C levels, since this method uniformly provides a lower coefficient of variation with respect to the values obtained for HDL-C, versus the method wherein only the CD absorption measurement at about 390 nm is used. The decrease in variation with the former method results from the fact that the effects of baseline drift are lessened when the algebraic sum of the two peaks is calculated.

In FIG. 1, band assignments were made by comparing the CD spectrum for the total cholesterol, curve (a) in FIG. 1, with the spectrum for the same sample after the selective precipitation of the low density lipid fractions with phosphotungstate-Mg, i.e., the shaded area in FIG. 1. The 525 nm band maximum was calibrated using NBS cholesterol (SRM 911a). Calibration of the 390 nm maximum was done using secondary HDL-C calibrators supplied by Sigma Chemical Co.

As an example of carrying out one of the methods of the present invention and determining the amounts of cholesterol fractions in a test sample, there is provided the following experimental Example:

EXPERIMENTAL EXAMPLE (a) Calibration of the CD instrument: a 50 μL aliquot of a $5 \times 10^{-3}$M solution of (SRM 911a) cholesterol in AR grade chloroform is placed in a vial of 10 mL total volume. 2.00 mL of the zinc chloride reagent are added and the mixture carefully shaken. 1.00 mL of acetyl chloride is added with care, the mixture shaken, and the vial capped and incubated at 67° C. for 8 minutes. The vial is removed and cooled quickly under water. Chloroform (1.00 mL) is then added to increase the solution volume in the vial. Such an addition of chloroform may be deleted if desired, if the CD analyzer will accommodate a 2.00 mL sample volume, or alternatively, an appropriate solvent substituted therefor. The solution is next transferred to a 1 cm pathlength cuvette and the CD spectrum run from 625-325 nm. The spectrum is corrected on a daily basis for the cell blank and the instrument baseline by subtracting the spectrum for the reagent mixture alone.

(b) Calibration of the CD Spectra: the procedure in (a) is repeated for a number of solution concentrations chosen to coincide with the typical range of serum cholesterol levels in the test sample. From the resultant calibration curve the proportionality constant relating the signal size at 525 nm to the (VLDL+LDL)-C level is 1.62 millidegrees per 100 mg/dL. The calibration at 390 nm was done in the same way, but the pure cholesterol was substituted by Sigma HDL-C calibrators. The signal size to HDL-C level at 390 nm is 2.08 millidegrees per 100 mg/dL.

(c) Cholesterol Determination in Clinical Test Samples by CD: the procedure in (a) is repeated for 50 µL aliquots of serum. Before being transferred to the cuvette, the specimen is centrifuged at high speed for 2 minutes. The (VLDL+LDL)-C fraction is calculated from the measured signal height at 525 nm and the HDL-C fraction from the signal height at 390 nm. Their sum gives the total cholesterol in the specimen. Selective precipitation of the low density fraction in order to measure the HDL-C fraction is not necessary in routine measurements. It is possible therefore, to do a cholesterol-lipid profile with a volume as little as a finger stick, and get the best precision yet obtained in the measurement of low density lipid fractions.

It should be noted that the reagents can be added in the order indicated in (a) Calibration of the Instrument. However, they can also be added simultaneously as a premixed solution or they can be added in the reverse order, e.g. add the acetyl chloride first, followed by the $ZnCl_2$ reagent. The latter mode of reagent addition had the unexpected effect of reducing the amount of precipitation in the test sample, thereby greatly reducing the scattering of incident light and thereby simplifying the subsequent measurement of absorption either by CD or by conventional spectroscopic absorption. An alternative is to use a reagent comprising zinc acetate (in lieu of zinc chloride in glacial acetic acid) and acetyl chloride.

Figure 2:
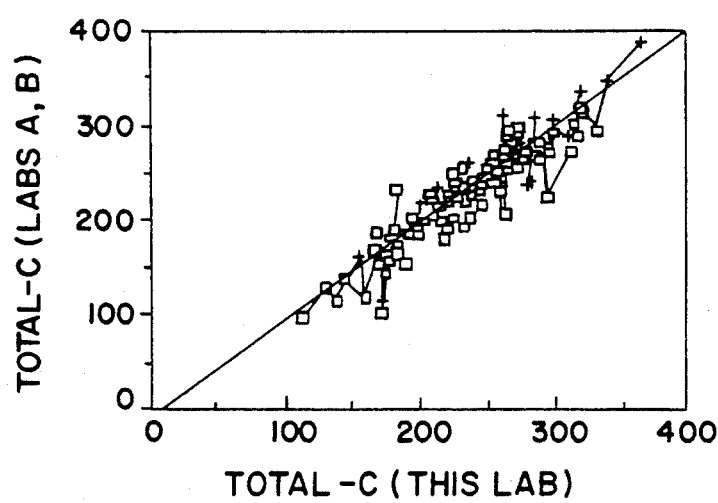
FIG. 2 represents the correlation between TC as measured in serum samples processed by two different labs using prior art processes (Labs A and B), versus total cholesterol as measured by the CD method of the present invention (This Lab); $y = -10.209 + 1.0055x$, $R^2 = 0.835$.

(d) Results of Exploratory Work: Cholesterol determinations were made on serum samples provided by two different laboratories, which employ the commercial methods developed by Abbott Laboratories (Lab A) and DuPont (Lab B), respectively. The correlations for total cholesterol levels are excellent, FIG. 2, and well within the limits imposed by the LSP.

Figure 3A:
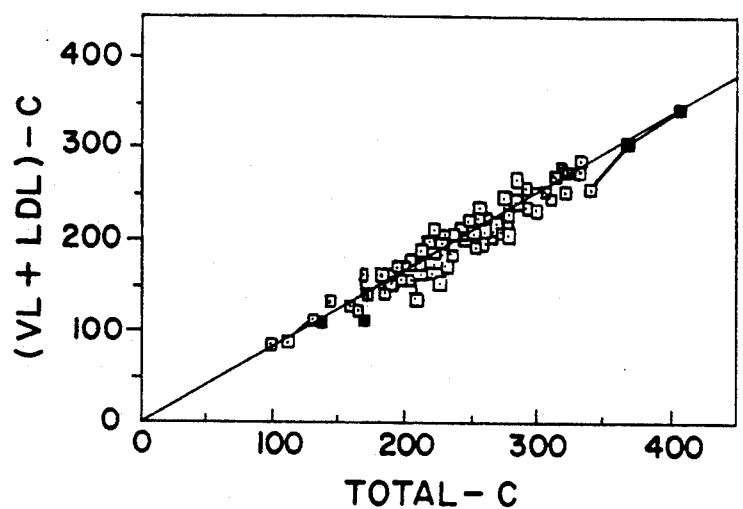
FIG. 3(a) is a graph of TC vs.(VLDL+LDL)-C using a CD method of the present invention (this lab); $y = 5.0554 + 0.84693X$, $R^2 = 0.932$.
Figure 3B:
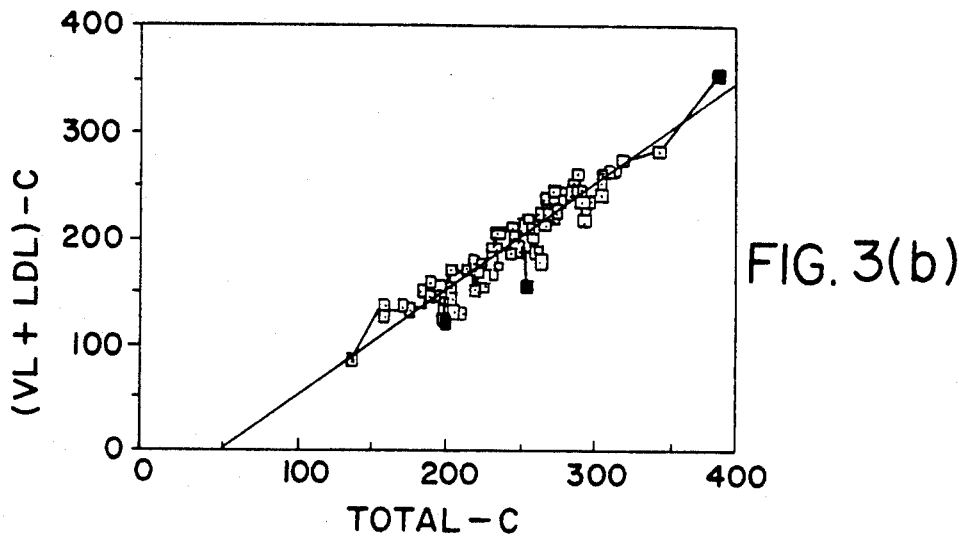
FIG. 3(b) is a graph of TC vs.(VLDL+LDL)-C using a prior art process (LAB-A); $y = -47.672 + 0.98751x$, $R^2 = 0.987$.
Figure 3C:
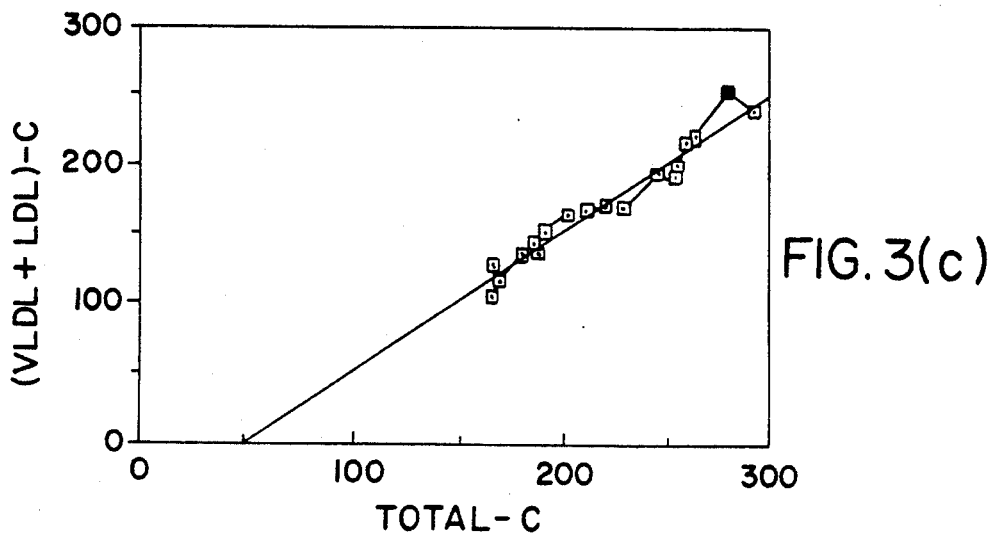
FIG. 3(c) is a graph of TC vs.(VLDL+LDL)-C using a prior art process (LAB-B); $y = -46.5222 + 0.9869x$, $R^2 = 0.98$.
Figure 4A:
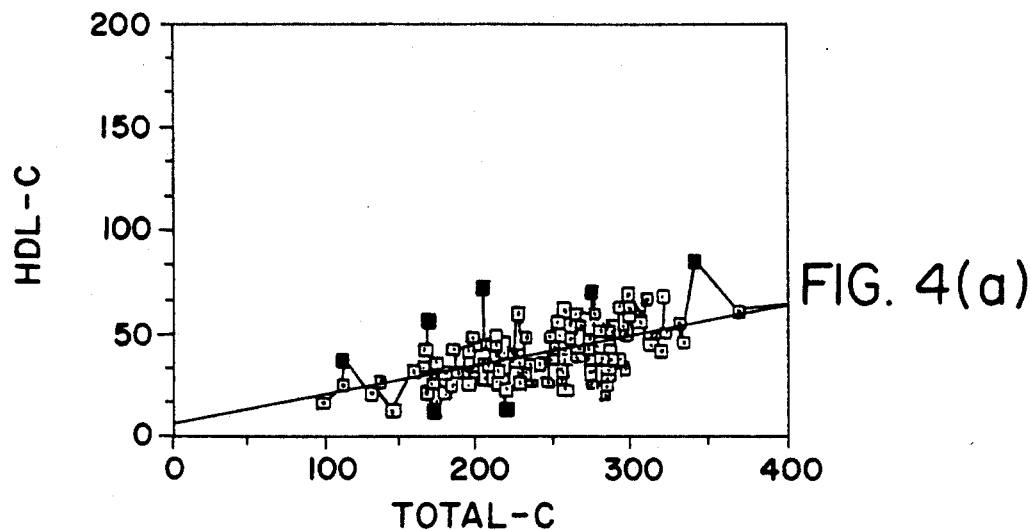
FIG. 4(a) is a graph of TC vs. HDL-C using the CD method of the present invention (this lab); $y = 5.2861 + 0.14995x$, $R^2 = 0.335$.
Figure 4B:
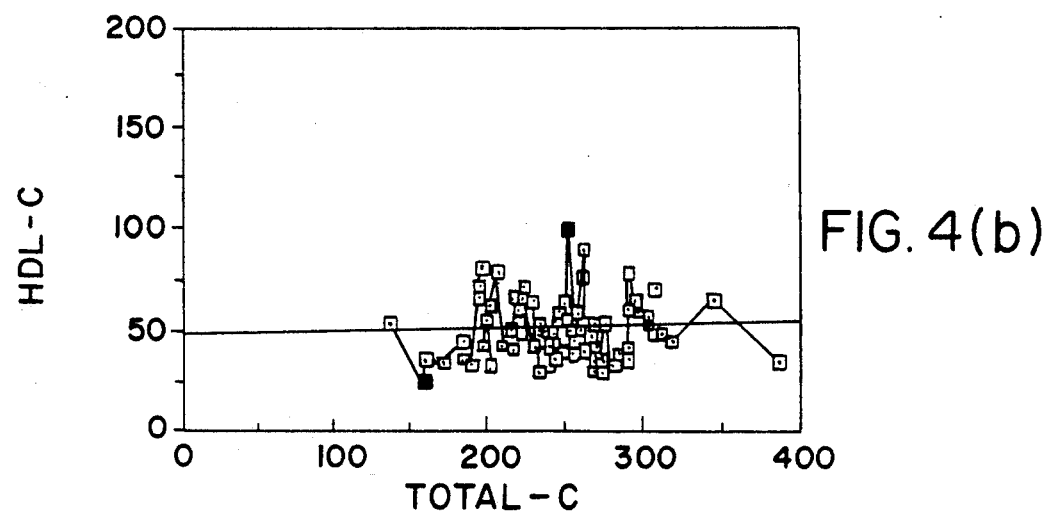
FIG. 4(b) is a graph of TC vs. HDL-C using a prior art process (LAB-A); $y = 47.648 + 0.012569x$, $R^2 = 0.001$.
Figure 4C:
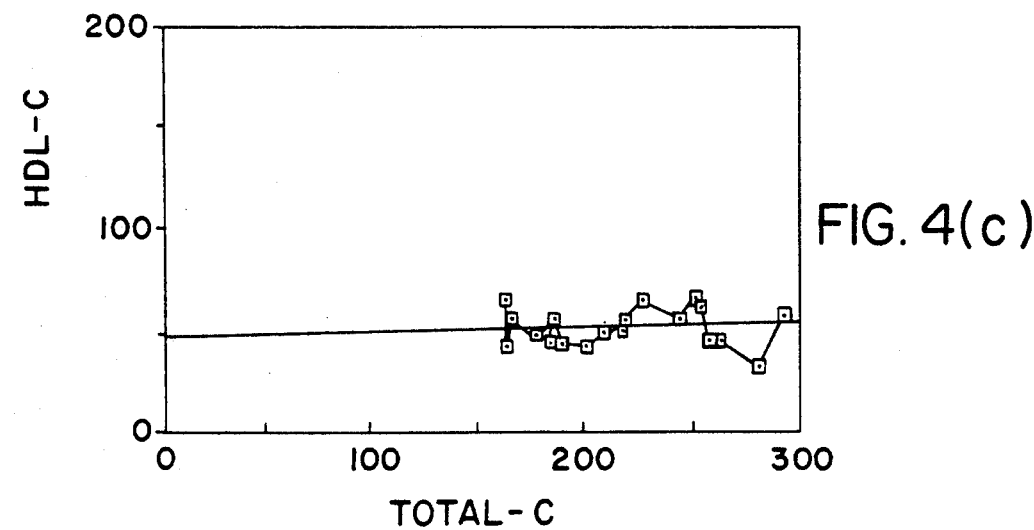
FIG. 4(c) is a graph of TC vs. HDL-C using a prior art process (LAB-B); $y = 46.522 + 0.0131x$, $R^2 = 0.06$.

A good case for believing that this new method is an improvement over prior methods, is to compare the correlations for the three data sets treated independently. Plots of total cholesterol versus (VLDL+LDL)-C are linear in every case, but there is a bias of almost 50 mg/dL in the intercepts on the x-axis for both conventional methods (FIGS. 3(b) and 3(c)) and zero correlation between the total and HDL-C data for these same data sets (FIGS. 4(b) and 4(c)). The Chugaev-CD data correlations by comparison, are excellent with low correlation intercepts, FIGS. 3(a) and 4(a), and the correlation slopes indicate that, for these sample populations, the "average" percentages for the HDL-C and (VLDL+LDL)-C fractions are 15% and 85%, respectively, which are in good agreement with the values normally accepted as typical for human serum distributions based upon ultracentrifugation data. Correlation slopes for the previously known spectrophotometric absorption methods are both one, which is not statistically possible, and which arises because the virtually constant measured value of 50 mg/dL for HDL-C is subtracted from measured TC values to obtain the results for (VLDL+LDL)-C.

(e) Accuracy and Analysis Time: Since there are no commercial reference standards for either LDL-C or VLDL-C, the accuracy cannot be evaluated. However, the precision and repeatability in the (VLDL+LDL)-C measurements are better than ±2%. With this level of precision, the confidence in one's ability to correlate the changes in LDL-C in reduction therapy studies, which involve diet and/or exercise modifications, is meaningfully improved.

The approximate time for a single analysis by the Chugaev-CD method with CD detection is about 15 minutes. While this is long compared to the commercial absorption methods used only for TC measurements, results for both low and high density fractions are obtained simultaneously. Because of the stability of the color, the turn around time can be reduced considerably by incubating several samples at once. With greater incident light intensities, sample path lengths can be reduced from 1 cm and the measurements can be automated.

Utilizing Chugaev reagents in procedures such as those provided above, several National Bureau of Standards SRM total cholesterol standards were also examined. The three samples tested were listed in the NBS catalogue as (1951-1)(210.36±2.46 mg/dL total), (1951-2)(242.29±1.53 mg/dL total), and (1951-3)(281.97±1.83 mg/dL total). According to the NBS Certificate of Analysis, the serum was donated by the CDC. The figures in parentheses are those measured at NBS and they compare extremely well with the CDC determinations using the modified Abell-Kendall method. The figures that we obtained from the Chugaev reaction, by adding the CD absorption values for the two fractions (HDL-C and (VLD+LDL)-C) were 206 mg/dL, 241.1 mg/dL, and 286.6 mg/dL, respectively. These results clearly evidence the effectiveness of the present inventive methods in determining cholesterol levels directly and precisely.

In order to further evidence the effectiveness of the present inventive CD methods in determining levels of cholesterol subfractions in a test sample, additional experimental data are provided in Table I.

TABLE I

| Patient | Blood Fractions | | |
|---|---|---|---|
| | VL + LDL(Chug)[1] | HDL(Chug)[2] | HDL(enz)[3] |
| A | 126 | 31 | [63] |
| B | 165 | 28 | [46] |
| C | 220 | 33 | — |
| D | 237 | 34 | [55] |
| E | 199 | 29 | 32 |
| F | 188 | 39 | 36 |
| G | 249 | 36 | 43 |
| H | 199 | 34 | 25 |
| I | 144 | 28 | [53] |

TABLE I-continued

| Patient | VL + LDL(Chug)[1] | HDL(Chug)[2] | HDL(enz)[3] |
|---|---|---|---|
| J | 216 | 46 | 52 |
| K | 190 | 38 | 35 |
| L | 211 | 41 | — |
| M | 239 | 39 | — |
| N | 190 | 39 | [56] |
| O | 220 | 50 | — |
| P | 174 | 46 | 46 |
| Q* | 249 | 51 | 57 |
| Q* | 242 | 48 | — |
| R | 184 | 47 | [60] |
| S | 205 | 29 | 33 |
| T | 126 | 46 | 45 |
| U | 157 | 46 | 49 |
| U* | 163 | 41 | — |
| V | 94 | 31 | [86] |
| W | 293 | 38 | — |
| X | 239 | 47 | [84] |
| Y | 207 | 57 | 55 |
| Sigma 400 | 340 | 61 | — |
| Sigma H | 230 | 52 | — |

[1] VL + LDL(Chug) - Cholesterol subfraction VLDL-C + LDL-C using Chugaev reagents and taking CD absorption measurement at 575 nm.
[2] HDL(Chug) - Cholesterol subfraction HDL-C obtained using Chugaev reagents and taking algebraic sum of CD absorption measurements at 390 and 475 nm.
[3] HDL(enz) - subfraction HDL-C obtained using the enzymatic method designated by Lab(A) and Lab(B).
*Asterisk indicates test was performed on patient's serum using mixed Chugaev reagents stored 4 weeks at 40° C.
[ ] = brackets indicate HDL measurements which are substantially different from HDL measurements using other methods.

Of the experimental results shown in Table I, it is noted that 12 out of 20 values for each of the HDL-C(Chug) and HDL-C(enz) methods agree to within 10 mg/dL. Such results clearly help to evidence the accuracy of the present methods.

B. Direct Detection Using Spectrophotometric Absorption Detection

As noted above, use of the CD method did not permit separation of LDL-C from VLDL-C. However, careful observation of the properties of the separate subfractions when treated with variants of the Chugaev reagent suggested that conventional absorption spectroscopy might permit that separation. As noted below, conditions were developed such that absorption detection may be used as a preferred alternative to CD detection in the present invention, if so desired. When utilizing absorption detection, Chugaev reactions as discussed above may be utilized. However, other reagents capable of forming colored reaction products with cholesterol and its subfractions may also be utilized.

The visible absorption spectrum for the colored product of the Chugaev reaction with cholesterol or serum cholesterol shows a strong maximum around 518 nm, a minimum around 460 nm, with shoulders at wavelengths between 460 and 365 nm showing a fairly weak absorption maximum (FIG. 6). Additionally, the Chugaev reagent itself absorbs in the visible range and has a weak maximum in the 350-370 nm regions.

In order to ascertain the effectiveness of the present inventive spectrophotometric absorption detection methods, samples of separated HDL, VLDL, and LDL lipoprotein fractions were obtained from Sigma Chemical Company (Sigma; fractions separated by ultrafiltration) and from Oklahoma Medical Research Foundation (OMRF; subfractions separated by ultracentrifugation). The three subfractions were reacted separately with Chugaev reagents to give colored products which possess different absorption spectra in the visible range. Spectral correspondences between the fractions from the two different sources were excellent for the HDL and LDL samples. Correspondence for the VLDL subfractions were also good. The spectral differences between each of the subfractions is sufficient to enable the three cholesterol subfractions to be qualitatively determined simultaneously in a single experiment without resorting to a selective precipitation step. For purposes of this example, absorption measurements are taken at 518, 450 and 420 nm. The serum spectrum of any test sample is an aggregate of the weighted contribution from each subfraction.

The ability to calculate the amount of each cholesterol subfraction present in a test sample, is due to the inventors' initial postulation that all three subfractions absorb at every wavelength analyzed, so that the general equation for total absorbance $A_t$ of a serum test sample is given by the equation:

$$E_{HDL}[\text{HDL}] + E_{VLDL}[\text{VLDL}] + E_{LDL}[\text{LDL}] = A_T$$

In the above equation, the E coefficients denote the absorbances for each of the subscripted fractions normalized in appropriate units of absorbance/(mg/dL), and the concentration terms [ ] are in mg/dL. Utilizing the above equation, and making the further assumption that each subfraction has the same or a substantially similar absorption coefficient at 518 nm but, as exemplified by the different spectra, have different absorption coefficients at the other wavelengths (in this case 420 and 450 nm), it is possible to calculate the amount of each subfraction present in a test sample by taking an $A_T$ measurement at each of the three discrete wavelengths in the spectrum and solving the resulting 3·3 matrix equation. In order to do this, the individual values for the subscripted E coefficients have to be determined for the three wavelengths selected. Relative values for the E coefficients at different wavelengths were easily obtained within the spectrum of any one of the subfractions. Relating these to the values of the equivalent wavelengths for the other fractions was more difficult, but was achieved and is disclosed herein. In this respect, spectral analysis of about 90 serum samples showed that a direct linear correlation existed between the $A_T$ values measured at 518 nm and the value for total cholesterol (TC) measured in a completely independent study that utilized a conventional method (data from Roche Laboratories). Based on this linear correlation, the inventor presupposed that a normalized value expressed as $A_T$/TC should be constant from sample to sample.

In order to correlate E values between the spectra for the different subfractions, the inventor postulated that the $A_T$/TC (or E) values at 518 nm are the same for all three subfractions, as noted above, and that the remaining six E coefficients for the three subfractions can be calculated for the remaining two wavelengths using simple proportions (e.g., $E_{LDL(420)} = A_{T(420)}/A_{T(518)}) \times E_{LDL(518)}$).

The amount of the above three lipofractions calculated from 60 serum samples utilizing the above technique and 3·3 matrixes provided results in excellent agreement with numbers obtained for the same test samples utilizing a conventional reaction procedure.

The specific test procedure utilized with the 60 samples that gave excellent agreement was as follows. After reagents were added the mixtures were allowed to incubate for 8 minutes at 67° C, thereafter cooled in a waterbath, centrifuged, transferred to a one cm cuvette, and a conventional absorption spectrum run from 700–400 nm. Absorption measurements were taken at 518, 450 and 420 nm, after appropriate corrections for the cell blank and the instrument base line were made. It is not necessary to run the entire spectrum, since absorbance measurements are only needed at the prescribed wavelengths. The nine E values for the wavelengths 518, 450 and 420 nm, respectively, obtained under the above described particular experimental conditions in units of absorbance, dL/gram were as follows: 3.05, 1.97, and 2.52 for HDL; 3.05, 1.35 and 2.41 for VLDL; and 3.05, 1.31 and 1.34 for LDL.

As noted previously, the use of conventional Chugaev reagents in absorption spectrophotometry gives rise to several problems which do not exist when they are used in CD methods. Specifically, whenever an absorption detection spectrophotometric method is utilized with Chugaev reagents precipitation may create problems. In order to fully minimize such problems, the Chugaev reagent should be modified such that either the ratio of acetyl chloride to zinc reagent is from 100:1 to 4:1 or zinc acetate is substituted for zinc chloride/acetic acid. The final zinc concentration should be between 0.03 and 0.22 molar. This is a composition much different from the reagent described in the literature (11).

It is noted that excellent absorption spectra have been obtained for volumes of serum as little as 2 μl. Likewise, excellent spectra were obtained for various acetyl chloride to serum ratios over the general broad range of 100:1 to 20:1 at constant zinc concentrations, and for acetyl chloride to zinc reagent ratios from 100:1 to 4:1 at constant serum amounts. Measurements have also been made with test samples, wherein the total reaction volume was as little as 0.15 mL and in cuvettes having a pathlength as short as 1 mm. Moreover, incubation times as little as two minutes have been achieved with the smaller total volumes, and it is fully envisioned that under conditions where serum concentrations are relatively high, that lower incubation temperatures may be utilized. Furthermore, with appropriate miniaturization, centrifugation may be eliminated.

In addition to the Chugaev reagent system described above, it is noted that ACS reagent grade zinc acetate dihydrate readily dissolves in acetyl chloride to a concentration that is similar to the final zinc ion concentration when added as the chloride in glacial acetic acid. Zinc acetate in acetyl chloride therefore can work, if desired, as a single reagent system. For example, if one mL of such a reagent system is added to 10 μL of a test serum, there is obtained a reddish-orange product after the usual incubation conditions. The maxima and minima in the spectra are at the same wavelengths but the ratios of the heights of these bands are different from those seen with the zinc chloride reagents, with the unexpected finding of a greater difference between the absorbances at 420 and 450 nm. Consequently, new E coefficients would need to be calculated for a 3·3 matrix if the zinc acetate were used rather than zinc chloride in acetic acid. The greater difference at those wavelengths means better precision in the values obtained for the subfractions. Indeed, the coefficients are highly dependent on the composition of the reagent and must be recalculated if the amounts of any of the reagent components are changed. However, such a calculation is in line with those earlier described, and clearly within the skill of those of ordinary skill in the art, based on the present disclosure.

A broad range of alternative reaction conditions to those reaction conditions discussed above, will produce reddish-orange colored products which have spectra that are similar, but not always equivalent to the absorbance spectrum of the species produced under the exact conditions utilized herein (as described above). Even so, when those skilled in the art utilize such alternative reaction conditions in combination with the 3·3 matrix strategy provided herein, and calculate the amounts of each subfraction present, they are practicing the inventor's presently disclosed methods. This is true, even though the nine E coefficients utilized may have to be revised after a recalibration of the spectra for standards of each of the subfractions (e.g., Sigma or OMRF provided subfractions) based on the exact reaction conditions employed. At such, it is envisioned that the present spectrophotometric methods clearly cover all such possible reagent mixtures and reagent ratios, so long as a colored reaction product is formed with the cholesterol subfractions, and the amounts of each subfraction are then determined in a manner as described above.

The above described spectrophotometric absorption methods offer an opportunity for simultaneous, on-line detection of cholesterol and cholesterol subfractions in clinical samples. The use of spectrophotometric absorption methods using such Chugaev reagents also permits much greater sensitivity than the CD methods herein disclosed allow for, since only a very small portion of the incident light can be used for CD signal generation. As such, the spectrophotometric absorption methods herein disclosed also permit the use of smaller volumes of sample, thereby reducing possible interferences caused by other materials and the total amount of precipitates formed by the reaction. Conversely, however, these reactions are more susceptible than CD to interferences from pigments released by hemolysis of the blood samples. Finally, it is important to note that, as with the CD studies mentioned above, addition of the acetyl chloride to the sample first, followed by addition of the $ZnCl_2$/acetic acid reagents reduces even further the interferences caused by precipitation in a clinical sample. Indeed it is possible to carry out spectrophotometric absorbance reactions in the present inventive methods using whole blood samples.

In the following Table II, there is provided comparative data obtained with test samples using both the spectrophotometric absorption/Chugaev method disclosed herein and an enzymatic method for the cholesterol subfractions shown. As may be seen upon review of Table II, excellent results were obtained using the Chugaev reagents/spectrophotometric absorption method herein described (as verified by comparing with results obtained on the same test samples using the enzymatic method).

TABLE II

| Subfractions from Enzymatic and Chugaev Methods | | | | | |
|---|---|---|---|---|---|
| Test Subject | Test | VLDL-C | LDL-C | HDL-C | TC |
| 1 | enzymatic | 32 | 155 | 28 | 216 |
|   | Chugaev | 29 | 155 | 35 | 222 |
| 2 | enzymatic | 46 | 178 | 37 | 262 |
|   | Chugaev | 50 | 173 | 42 | 264 |
| 3 | enzymatic | 37 | 110 | 36 | 183 |
|   | Chugaev | 48 | 103 | 31 | 182 |
| 4 | enzymatic | 34 | 133 | 46 | 214 |
|   | Chugaev | 38 | 139 | 36 | 213 |
| 5 | enzymatic | 42 | 155 | 45 | 242 |

TABLE II-continued

| Subfractions from Enzymatic and Chugaev Methods | | | | | |
| --- | --- | --- | --- | --- | --- |
| Test Subject | Test | VLDL-C | LDL-C | HDL-C | TC |
| | Chugaev | 44 | 161 | 41 | 246 |
| 6 | enzymatic | 62 | 113 | 26 | 202 |
| | Chugaev | 65 | 101 | 35 | 203 |

Based on the above considerations, there is provided herein a novel spectrophotometric absorption detection method, wherein Chugaev reagents are reacted with cholesterol subfractions in clinical samples so that a direct measurement of the cholesterol subfractions can be made. The measurements can be made either as a full spectrum over the range of about 150–700 nm or at 3 selected wavelengths, in this case about 420 nm, 450 nm, and 518 nm.

The major procedural difference between the absorption and the CD method relates to the standards used. While cholesterol itself can be used as a standard for the CD reactions, clinical standards for TC and cholesterol subfractions obtained from the CDC, CAP or a commercial source must be used to calibrate the absorption spectrometer.

Further to the above disclosed spectrophotometric methods, given the availability of "pure" samples of VLDL-C, LDL-C and HDL-C, a mathematical algorithm can be prepared, if so desired, which enables one to add the individual subfractions' spectrophotometric absorption spectra in a weighted fashion for each subfraction. In such a manner the total absorption spectrum for the test sample is obtained. Utilizing such a method would be analogous to measuring the spectrophotometric absorption of a colored reaction product at an infinite number of points, instead of just at three or more distinct points as described above.

Figure 7B:
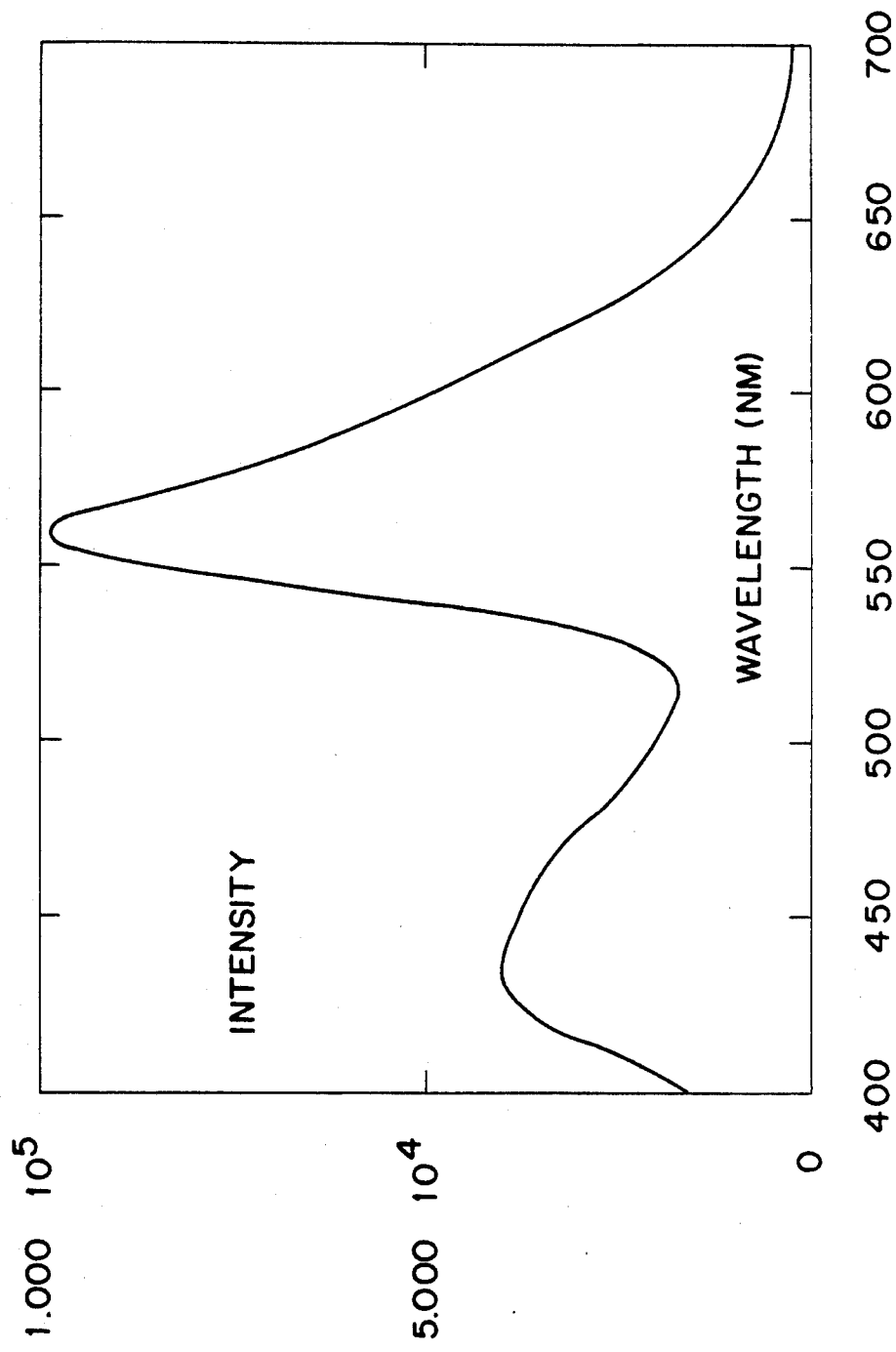
FIG. 7(b) is a graph of the fluorescence spectrum for LDL-C subfraction.

C. Direct Detection Using Fluorescence and Derivative Absorption Spectrophotometric Methods The products of the reaction of cholesterol with the Chugaev reagents are fluorescent. Moreover, fluorescence spectra for the three lipoprotein subfractions VLDL-C, LDL-C and HDL-C are different from each other and from the spectrum for a serum sample (see FIGS. 7(a), 7(b) and 7(c)). The mathematical analysis of fluorescence data, wherein one calculates the amounts of each of the subfractions present in a serum test sample is entirely equivalent to that described above for the conventional absorbance detection spectrophotometry. All that is required to initiate the calculation are the nine fluorescence coefficients for whatever three wavelengths are selected in the fluorescence spectrum for serum. In this respect, wavelengths different from those utilized in conventional absorption spectrophotometry are needed, since the maximum and minimum wavelengths for fluorescence occur at longer wavelengths.

Figure 8A:
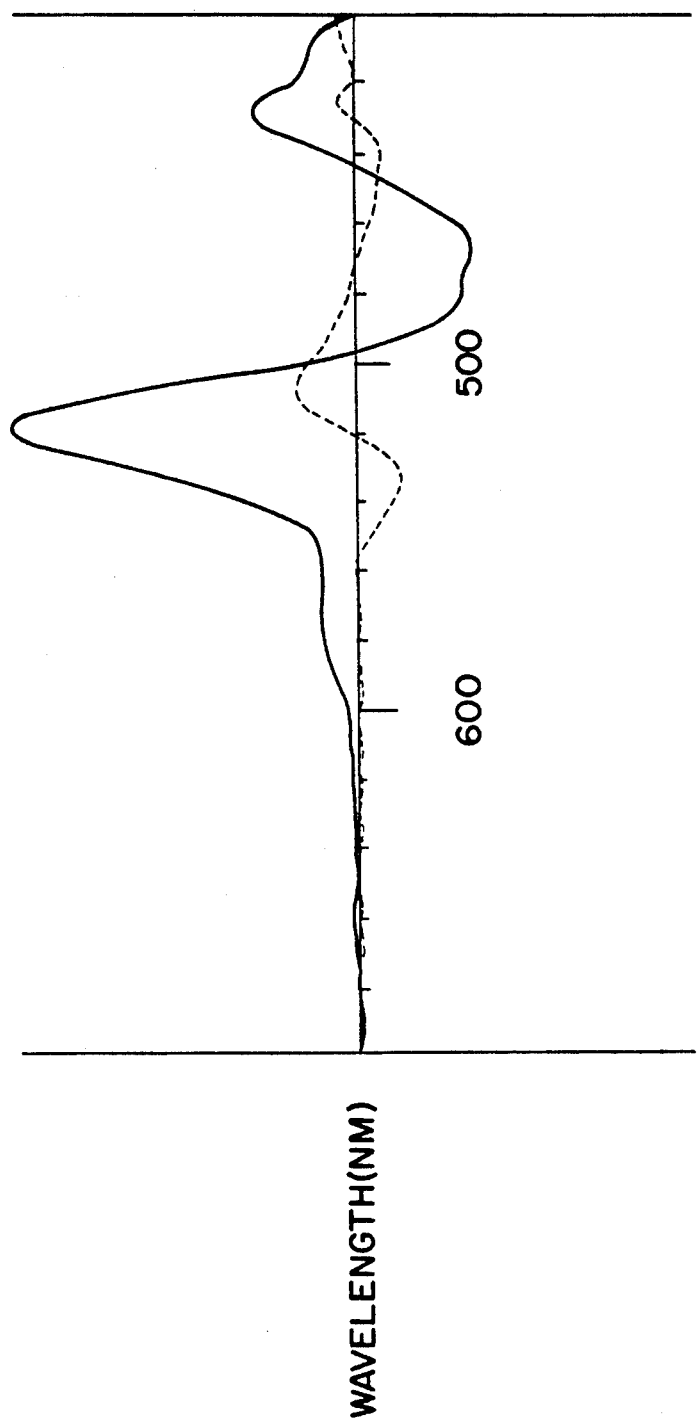
FIG. 8(a) is a graph of the first (solid line) and second (dotted line) derivatives of the conventional absorbance spectrum of the VLDL-C subfraction (sigma)
Figure 9A:
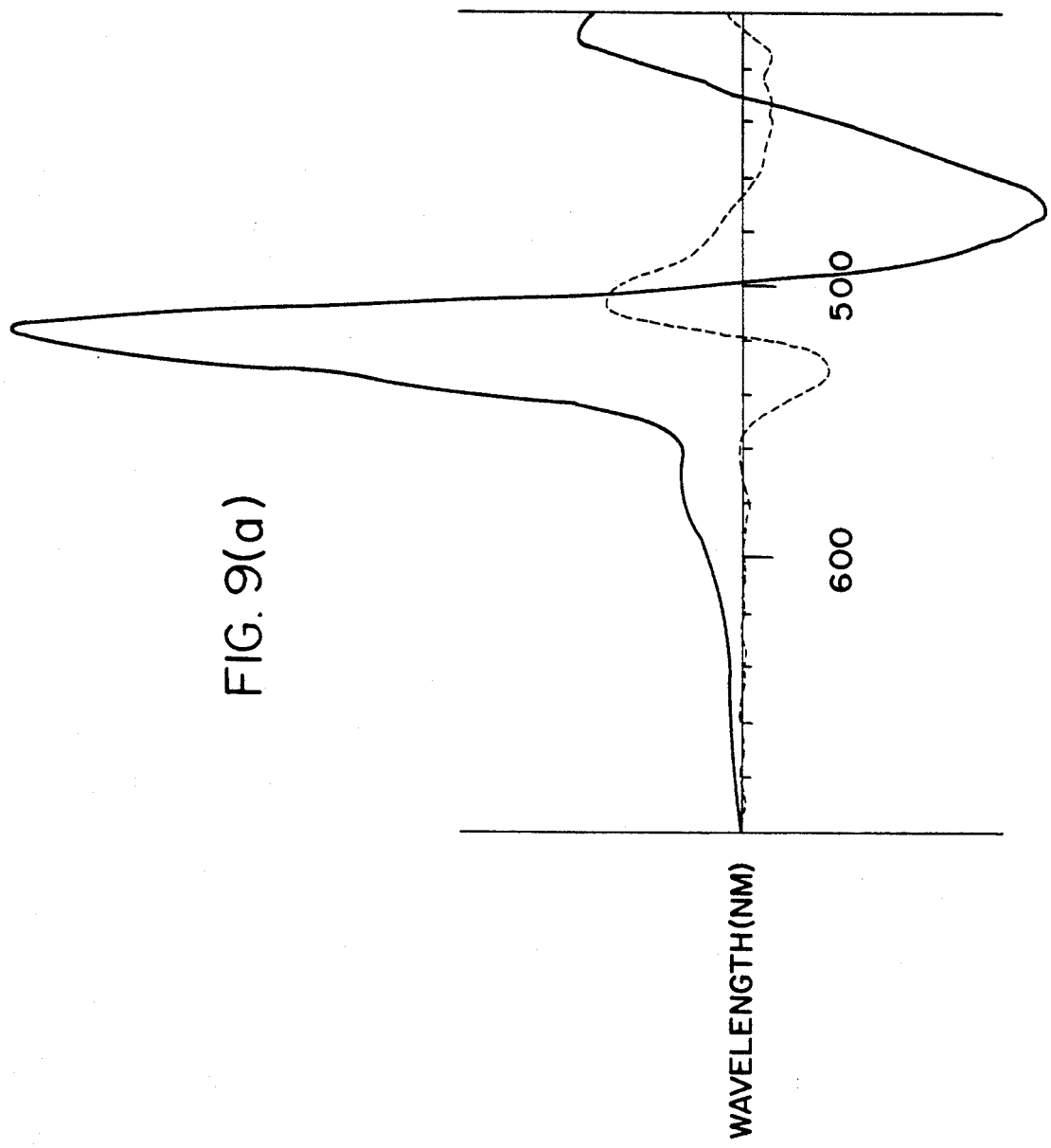
FIG. 9(a) is a graph of the first (solid line) and second (dotted line) derivatives of a serum A test sample.

Similarly, derivative absorption spectrophotometry may also be utilized to calculate the amount of a cholesterol subfraction present in the test serum sample. For example, first and second derivatives of absorbance spectra can be utilized for analytical measurements. Copies of derivative absorbance spectra for each of the three lipoprotein subfractions are shown in FIG. 8. FIG. 8(a) shows the first and second derivative for VLDL-C; FIG. 8(b) shows the first and second derivative for LDL-C; and FIG. 8(c) shows the first and second derivative for HDL-C. In each of FIGS. 8(a)–8(c), the solid line denotes a first derivative of the absorbance spectrum and the dotted line denotes the second derivative of the absorbance spectra. Each of the subfractions utilized to obtain the graphs 8(a)–8(c) were obtained from Sigma Chemical Co. When utilizing derivative absorption spectrophotometry, subtle differences exist between the spectra for each of the fractions. Again, the mathematical analysis is completely analogous to that discussed above for absorbance detection and fluorescence spectrophotometries. However, three new wavelengths would need to be chosen. Signal intensities at the band maxima are much better separated than with other methods and precision may therefore be increased. In two measurements on serum samples (see FIGS. 9(a) and 9(b)) it was determined that the peak to peak heights for the two major bands were directly proportional to TC. Data collection utilizing derivative spectrophotometry requires the use of a full spectrum analysis.

INVENTIVE APPARATUS

Upon review of the above methods section, it can be easily ascertained that the present inventive methods have many advantageous attributes when compared with presently known methods for determining cholesterol levels in test samples. However, the present invention also encompasses novel instruments, which allow those skilled in the art to practice the present inventive methods. Such inventive instruments are outlined above (see Section entitled "Summary of the Invention").

A spectrophotometric instrument encompassed hereby should be equipped with 1 or more spectrophotometric absorption detectors capable of measuring the absorption of the colored products of the Chugaev reagent over a range of from about 360–700 nm, or at discrete points therein such as about 518 nm, 450 nm and 420 nm. If automated, it should also have the capability of adding the Chugaev reagents to separate sample containers for analysis or to sequentially add the components of the Chugaev reagents to minimize problems due to precipitation of proteins. Finally, any such absorption spectrophotometer, manual or automatic, should preferably have the means to determine the levels of each subfraction present in a serum test sample by a calculation or computation from the absorption values obtained. Specifically, the instrument should have the ability to compute the results of the 3·3 matrix, with nine pre-programmed constants, to establish the levels of VLDL-C, LDL-C and HDL-C present, and to use these values to compute the TC present in the sample.

It should be noted that the 3·3 matrix represents the minimum possible to measure the three subfractions. It is possible that finer analysis of the spectrum produced by the reagent will indicate that constants at other specific wavelengths will provide useful information, e.g., about specific molecular entities within the various subfractions. In that case, the instrument should be constructed to analyze matrixes larger than 3·3.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

REFERENCES

1. Lambert, J. B., Shurvell, H. F., Verbilt, L. Cooks, R. G., and Stout, G. H., "Organic Structural Analysis", Macmillan, New York, N.Y. 1976.
2. Grahnen, A., Sjoholm, I., and Michaëlsson, M., Clinica Chimica Acia, 52, 187–196 (1974).
3. Kannel, W. B., Castelli, W. P., Gordon, T. et al, "Serum cholesterol, lipoproteins, and the risk of coronary heart disease: The Framingham Study", Ann. Intern.Med. 1971; 74:1–11.
4. Castelli, W. P., Garrison, R. J., Wilson, W. F., Abbott, R. D., Kalousdian, S., Kannel, W. B., "Incidence of coronary heart disease and lipoprotein cholesterol levels", JAMA 1986, 256:2835–2838.
5. Abbott, R. D., Garrison, R. J., Wison, P. W. F. et al, "Joint distribution of lipoprotein cholesterol classes, The Framingham Study", Arteriosclerosis 1983, 3:260–272.
6. Laboratory Standardization Panel, NCEP, "Current status of blood cholesterol measurement in clinical laboratories of the United States, A report from the Laboratory Standardization Panel of the National Cholesterol Education Program", Clin.Chem. 1988, 34:193–201.
7. Superko, H. R., Bachorik, P. S., Wood, P. D., "High-density lipoprotein cholesterol measurements—A help or hindrance in practical clinical medicine?" JAMA 1986, 256: 2714–2717.
8. Posnick, L., "Labs now better at cholesterol tests, data show", reported in Clin.Chem.News 1989; 15(9):14.
9. Warnick, G. R., Albers, J. J., Teng-Leary, E., "HDL cholesterol: Results of interlaboratory proficiency test." Clin.Chem. 1980; 26:169–170.
10. Grundy, S. M., Goodman, D. W., Rifkind, B. M., Cleeman, J. I., "The place of HDL in cholesterol management. A perspective from the national cholesterol education program." Arch.Inter.Med. 1989; 149:505–510.
11. Cox, R. H. and Spencer, E. Y., Can. J. Chem., 29, 217 (1951).
12. KatZung, B. G., "Basic and Clinical Pharmacology, 4th Ed.", p. 419–421, Appleton & Lange, Englewood Cliffs, N.J. (1989).
13. Baillie, E. G., Leary, E. T., Warnick, G. R. & Wiebe, D., "Standardization and Clinical Utility of Lipid Determinations", Workshop, 43rd National Meeting, American Association for Clinical Chemistry, 1991.
14. Warnick, G. R., "Standardization of HDL Cholesterol Measurement" Roundtable, 43rd National Meeting, American Association for Clinical Chemistry, 1991.

What is claimed is:

1. A clinical detection method for determining the amount of cholesterol present in a test sample, the method comprising:
   (a) forming an optically active, colored reaction product with said cholesterol present in the test sample wherein said colored reaction product is formed by reacting a Chugaev reagent with said cholesterol, and wherein zinc is present in the Chugaev reagent at a final concentration of 0.03 to 0.22 molar;
   (b) determining the CD absorption spectrum of said test sample over the continuous range of from about 150 nm to about 700 nm; and
   (c) determining the amount of cholesterol in the test sample based on the CD absorption of the test sample in step (b).

2. The detection method recited in claim 1, wherein the Chugaev reagent comprises:
   zinc acetate and acetyl chloride.

3. The detection method recited in claim 1, wherein the Chugaev reagent comprises:
   zinc chloride, glacial acetic acid and acetyl chloride.

4. The detection method recited in claim 1, wherein the reaction product is formed by combining the following Chugaev reagent components sequentially with the test sample:
   (1) acetyl chloride, and then
   (2) zinc chloride in glacial acetic acid.

5. The detection method as recited in claim 1, wherein the amount of cholesterol present in the test sample is distributed among a HDL-C subfraction and a (LDL-C+VLDL-C) subfraction, and is determined based on the test sample's CD absorption in step (b) at two or more wavelengths in the continuous range of from about 150 to about 700 nm, one of which wavelengths is about 525 nm.

6. The detection method recited in claim 5, wherein the amount of cholesterol present in the HDL-C subfraction is determined based on the test sample's CD absorption in step (b) at a wavelength of about 390 nm.

7. The detection method recited in claim 5, wherein the amount of cholesterol present in the HDL-C subfraction is determined based on the test sample's CD absorption in step (b) at a wavelength of about 475 nm.

8. The detection method recited in claim 5, wherein the amount of cholesterol present in the HDL-C subfraction is determined by calculating the algebraic sum of the test sample's CD absorption in step (b) at two distinct wavelengths of about 390 nm and about 475 nm.

9. A detection method for determining the amount of cholesterol present in a test sample, the method comprising:
   (a) forming an optically active, colored reaction product with said cholesterol present in the test sample, wherein said colored reaction product is formed by reacting a Chugaev reagent with said cholesterol, and wherein zinc is present in the Chugaev reagent at a final concentration of 0.03 to 0.22 molar;
   (b) determining the CD absorption spectrum of said test sample at two or more discrete wavelengths within a range of from about 150 nm to about 700 nm; and
   (c) determining the amount of cholesterol in the test sample based on the CD absorption of the test sample in step (b).

10. The detection method recited in claim 9, wherein the Chugaev reagent comprises:
    zinc acetate and acetyl chloride.

11. The detection method recited in claim 12, wherein the Chugaev reagent comprises:
    zinc chloride, glacial acetic acid and acetyl chloride.

12. The detection method recited in claim 9, wherein the amount of cholesterol present in the test sample is distributed among a HDL-C subfraction and a (LDL-C+VLDL-C) subfraction, and is determined by measuring the test sample's CD absorption at two or more wavelengths of from 150 to 700 nm, one of which wavelengths is about 525 nm.

13. The detection method recited in claim 12, wherein the amount of cholesterol present in the HDL-C subfraction is determined by measuring the test sample's CD absorption at a wavelength of about 390 nm.

14. The detection method recited in claim 12, wherein the amount of cholesterol present in the HDL-C subfraction is determined by measuring the test sample's CD absorption at a wavelength of about 475 nm.

15. The detection method recited in claim 12, wherein the amount of cholesterol present in the HDL-C subfraction is determined by calculating the algebraic sum of the test sample's CD absorption at wavelengths of about 390 nm and about 475 nm.

16. The detection method as recited in claim 12, in which the test sample's HDL-C and LDL-C+VLDL-C levels are determined by CD absorption, and then the test sample's total cholesterol level is determined by summing the HDL-C and LDL-C+VLDL-C levels which were determined by CD absorption.

17. The detection method as recited in claim 12, wherein the test sample's HDL-C and LDL-C+VLDL-C levels are determined by CD absorption, and then the test sample's total cholesterol level is determined by spectrophotometric absorption.

18. The detection method as recited in claim 17, wherein the test sample's total cholesterol level is determined by spectrophotometric absorption, and is then compared with a total cholesterol level for the test sample which is determined by summing the LDL-C+VLDL-C and HDL-C levels which were determined by CD absorption.

19. A detection method for determining the levels of VLDL-C, LDL-C, HDL-C and total cholesterol present in a test sample, the method comprising:
   forming a colored reaction product with said cholesterols by reacting a Chugaev reagent with said test sample, and measuring the spectrophotometric absorption of said reaction product at three or more distinct wavelengths within the range of about 150 nm to 700 nm, and thereafter calculating the amount of the VLDL-C, LDL-C, HDL-C and total cholesterol present in the test sample based on the reaction product's measured spectrophotometric absorption at the distinct wavelengths.

20. The detection method recited in claim 19, wherein the Chugaev reagent comprises:
   acetyl chloride, zinc chloride and acetic acid.

21. The detection method recited in claim 19, wherein the Chugaev reagent comprises:
   zinc acetate and acetyl chloride.

22. The detection method recited in claim 19, wherein zinc is present in the Chugaev reagent at a final concentration of from 0.03 to 0.22 molar.

23. The detection method as recited in claim 19, wherein the colored reaction product is formed by combining the following Chugaev reagent components sequentially with the test sample to form the Chugaev reaction product:
   (1) acetyl chloride, and then
   (2) zinc chloride in glacial acetic acid.

24. The detection method recited in claim 19, wherein the amounts of the HDL-C, LDL-C and VLDL-C subfractions present in the test sample are determined by solving an n·n matrix, wherein n is the number of distinct wavelengths at which the reaction product's spectrophotometric absorption is measured.

25. The detection method recited in claim 24, wherein n is 3.

26. The detection method recited in claim 25, wherein the n·n matrix is solved using the reaction product's measured spectrophotometric absorptions at the distinct wavelengths, and an absorption constant for HDL-C, LDL-C and VLDL-C at each distinct wavelength.

27. The detection method as recited in claim 23, wherein the Chugaev reagent components are combined in a ratio of from about 100:1 to 4:1 of the acetyl chloride to the zinc chloride/acetic acid.

* * * * *